(12) United States Patent
Glocker

(10) Patent No.: US 9,649,449 B2
(45) Date of Patent: May 16, 2017

(54) SYRINGE HAVING TWO-PART CAP AND TUBULAR NECK SEALING NEEDLE PUNCTURE MEMBRANE

(75) Inventor: Joachim Glocker, Weingarten (DE)

(73) Assignee: ARZNEIMITTEL GmbH APOTHEKER VETTER & CO. RAVENSBURG, Ravensburg (DE)

( * ) Notice: Subject to any disclaimer, the term of this patent is extended or adjusted under 35 U.S.C. 154(b) by 1404 days.

(21) Appl. No.: 12/223,907

(22) PCT Filed: Feb. 7, 2007

(86) PCT No.: PCT/EP2007/001017
§ 371 (c)(1),
(2), (4) Date: Aug. 11, 2008

(87) PCT Pub. No.: WO2007/093307
PCT Pub. Date: Aug. 23, 2007

(65) Prior Publication Data
US 2010/0168678 A1 Jul. 1, 2010

(30) Foreign Application Priority Data
Feb. 14, 2006 (DE) .................. 10 2006 006 672

(51) Int. Cl.
A61M 5/315 (2006.01)
A61M 5/32 (2006.01)
(Continued)

(52) U.S. Cl.
CPC ............ *A61M 5/3202* (2013.01); *A61M 5/24* (2013.01); *B65D 51/002* (2013.01);
(Continued)

(58) Field of Classification Search
CPC ...... A61M 5/288; A61M 5/286; A61M 5/285; A61M 5/5086; A61M 2005/3104; A61M 5/24; A61M 5/31511; A61J 1/2096
(Continued)

(56) References Cited

U.S. PATENT DOCUMENTS 2,677,374 A * 5/1954 Burnside ................. A61M 5/28
604/199
3,424,155 A * 1/1969 Sarnoff ................. A61M 5/286
604/200
(Continued)

FOREIGN PATENT DOCUMENTS

DE 196 38 940 C2 4/1998
DE 101 02 054 A1 8/2002
(Continued)

OTHER PUBLICATIONS

Japanese Office Action (3 pages) mailed Nov. 15, 2011 for parallel application JP 2008-554628, with English translation thereof (4 pages).
(Continued)

*Primary Examiner* — Kami A Bosworth
*Assistant Examiner* — Matthew A Engel
(74) *Attorney, Agent, or Firm* — Stephen T. Olson; Harness, Dickey & Pierce, P.L.C.

(57) ABSTRACT

A syringe or carpule includes a cylinder that surrounds a cavity and comprises an end that has an access to the cavity, membrane seals the access and has a puncture area that can be punctured by a needle. A two-part cap has a predetermined breaking line and spans the membrane. A cover device covers the puncture area of the membrane in a sterile manner and comprises a sealing area spanning the puncture area. The sealing area covers the puncture area in a sterile
(Continued)

manner regardless of axial forces to be applied in the area of the predetermined breaking line.

3 Claims, 5 Drawing Sheets

(51) Int. Cl.
*A61M 5/24* (2006.01)
*B65D 51/00* (2006.01)
*A61M 5/31* (2006.01)
*A61M 5/50* (2006.01)

(52) U.S. Cl.
CPC ......... *A61M 5/2466* (2013.01); *A61M 5/5086* (2013.01); *A61M 2005/312* (2013.01)

(58) Field of Classification Search
USPC ................ 604/111, 199, 200, 205, 206, 232
See application file for complete search history.

(56) References Cited

U.S. PATENT DOCUMENTS

| | | | | |
|---|---|---|---|---|
| 3,739,779 | A * | 6/1973 | Pfleger | A61M 5/288 401/134 |
| 4,596,561 | A * | 6/1986 | Meyer | A61M 5/2429 604/190 |
| 5,067,948 | A * | 11/1991 | Haber | A61M 5/2448 604/192 |
| 5,135,514 | A | 8/1992 | Kimber et al. | |
| 5,320,603 | A * | 6/1994 | Vetter | A61M 5/284 604/416 |
| 5,342,346 | A * | 8/1994 | Honda | A61J 1/2089 604/411 |
| 5,803,284 | A | 8/1998 | Nakamura et al. | |
| 5,833,653 | A * | 11/1998 | Vetter | A61M 5/286 604/205 |
| 5,989,227 | A | 11/1999 | Vetter et al. | |
| 6,190,364 | B1 * | 2/2001 | Imbert | A61M 5/3134 604/111 |
| 6,196,998 | B1 * | 3/2001 | Jansen | A61M 5/3134 604/111 |
| 6,382,442 | B1 | 5/2002 | Thibault et al. | |
| 6,440,101 | B1 * | 8/2002 | Grabenkort | A61M 5/31596 604/122 |
| 6,520,935 | B1 * | 2/2003 | Jansen | A61M 5/3134 604/111 |
| 6,817,987 | B2 * | 11/2004 | Vetter | A61M 5/284 604/85 |
| 7,041,087 | B2 * | 5/2006 | Henderson | A61M 5/3134 604/200 |
| 7,645,267 | B2 * | 1/2010 | Vetter | A61M 5/28 604/218 |
| 7,731,679 | B2 * | 6/2010 | Tennican | A61J 1/2096 604/88 |
| 7,828,777 | B2 * | 11/2010 | Vetter | A61L 2/07 604/192 |
| 8,574,214 | B2 * | 11/2013 | Kuhn | A61M 5/288 604/411 |
| 2001/0001116 | A1 * | 5/2001 | Daubert | A61J 1/2096 604/200 |
| 2002/0123736 | A1 * | 9/2002 | Fowles | A61J 1/1406 604/413 |
| 2009/0131864 | A1 * | 5/2009 | Pickhard | A61M 5/284 604/83 |
| 2012/0248057 | A1 * | 10/2012 | Bogle | A61J 1/1406 215/43 |

FOREIGN PATENT DOCUMENTS

| | | |
|---|---|---|
| EP | 0 328 504 A1 | 8/1989 |
| EP | 0 832 822 A1 | 4/1998 |
| EP | 0 917 882 B1 | 5/1999 |
| JP | 2004-024441 | 1/2004 |
| WO | WO-88/00478 A | 1/1988 |

OTHER PUBLICATIONS

Canadian Office Action in the parallel procedure CA 2,644,486, mailed Jun. 17, 2015.

* cited by examiner

US 9,649,449 B2

SYRINGE HAVING TWO-PART CAP AND TUBULAR NECK SEALING NEEDLE PUNCTURE MEMBRANE

FIELD

The present disclosure relates to a syringe or carpule with a membrane and a cover device.

BACKGROUND

Syringes or carpules of the type discussed here are known. They have a cylinder that surrounds a cavity that is used to accommodate the syringe liquid, and an end that has an access to the cavity. A membrane seals the access in order to keep the liquid sterile in the cavity of the cylinder. This membrane is embodied such that it has a puncture area that can be punctured by a needle when the syringe or carpule is used.

It has proven that dirt particles can be deposited on the surface of the membrane facing away from the cylinder end during the storage of syringes or carpules of this type. These dirt particles can reach the syringe liquid and contaminate it when a needle punctures the membrane. In order to solve this problem, the end of the syringe cylinder is provided with a cover device that covers the needle puncture area of the needle in a sterile manner and that comprises a sealing area spanning the needle puncture area. With this cover device the membrane is protected from contamination during storage. Furthermore, the end of the cylinder has a cap spanning the membrane, which cap has a predetermined breaking line and is held on the cylinder. If the cap is to be detached from the cylinder before the puncture process, the cap or a part thereof can be easily detached via the predetermined breaking line. EP 0 917 882 B1 describes a safety cap that covers a membrane that is attached via a cap at the end of the cylinder. This cap is embodied in two parts, a first partial area covering the puncture area of the membrane and a second partial area being attached to the cylinder. Both partial areas are connected via a predetermined breaking line. The cap presses the cover device against the puncture area. The disadvantage is that axial tensions thus occur in the area of the predetermined breaking line that can lead to the predetermined breaking line bursting open during the storage of the syringe, the first partial area then detaching from the second partial area and the puncture area of the membrane being exposed.

SUMMARY

The object of the invention is therefore to create a syringe or carpule in which the membrane is covered in a sterile manner and no axial tensions are generated on the predetermined breaking line of the cap.

To attain this object a syringe or carpule is proposed characterized by a cover device, the sealing area of which covers the puncture area in a sterile manner regardless of axial forces to be exerted in the area of the predetermined breaking line.

An exemplary embodiment of the syringe or carpule is preferred that is characterized in that the sealing area comprises a sealing foil spanning the needle puncture area. This embodiment ensures that the membrane is covered in a sterile manner and no contaminants can reach the puncture area.

An exemplary embodiment is particularly preferred that is characterized in that the cover device has a projection and a recess accommodating the projection at least in some areas, and that the outer diameter of the projection is coordinated with the inner diameter of the recess such that the sealing area is formed by a radial seal. Since the seal is realized in a radial manner, no axial forces can occur that can burst open the predetermined breaking line during a storage of the syringe.

DRAWINGS

The invention is described in more detail below based on the drawing. They show:

DETAILED DESCRIPTION

Figure 1:
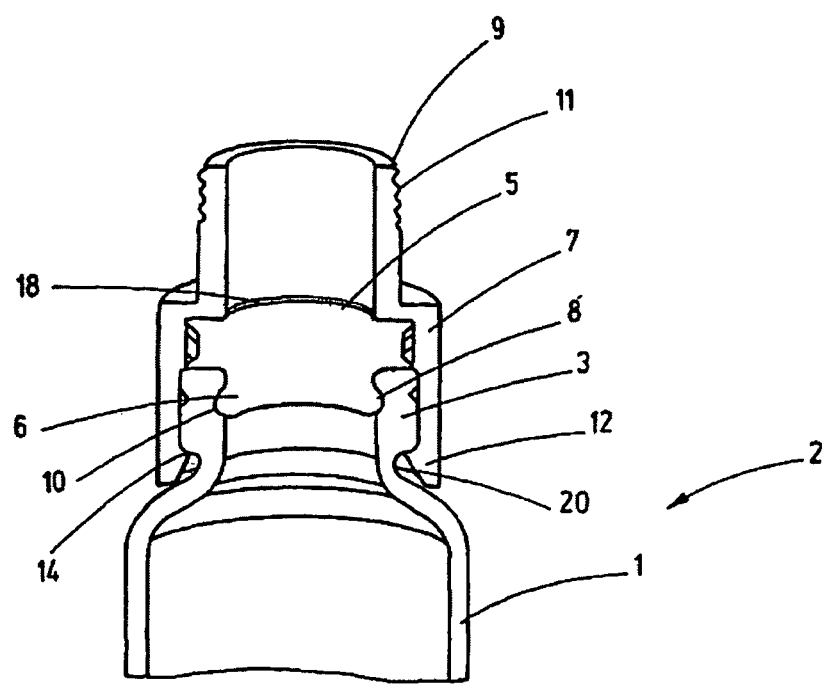
FIG. 1 is a longitudinal section of an end of a syringe cylinder without cover device.

FIG. 1 shows a longitudinal section through a cylinder 1 of a syringe 2 or carpule. A membrane 5 bears on one end 3 of the cylinder 1. This membrane seals the cylinder 1. Furthermore, on the side facing towards the cylinder 1, the membrane 5 has a projection 6 that engages in the interior of the cylinder 1. A radially projecting bead 8 is discernible on the surface of the projection 6, which bead engages in a recess 10 in the interior of the end 3. The membrane 5 is thus held at the end 3 of the cylinder 1. In addition, a closure element 7 is placed on the end 3 to fix the membrane 5. This closure element 7 wraps around the membrane 5 and the end 3 of the cylinder 1 and has at least one hook 14 on its end 12 facing toward the cylinder 1. This hook 14 engages in a recess 20 that is located between the end 3 of the cylinder 1 and the cylinder 1 itself. The closure element 7 is thus attached to the end 3 of the cylinder 1. The membrane 5 is located between the closure element 7 and the end 3. In addition, the closure element 7 has a lug 9. This lug 9 is hollow, embodied in a cylindrical manner, and is provided with an external thread 11. The closure element 7 does not cover the membrane 5 completely due to the lug 9 embodied in a hollow manner. The area of the membrane 5 that is not covered by the closure element 7, and which can be punctured by a needle when the syringe is used is called the puncture area 18 or needle puncture area.

Figure 2:
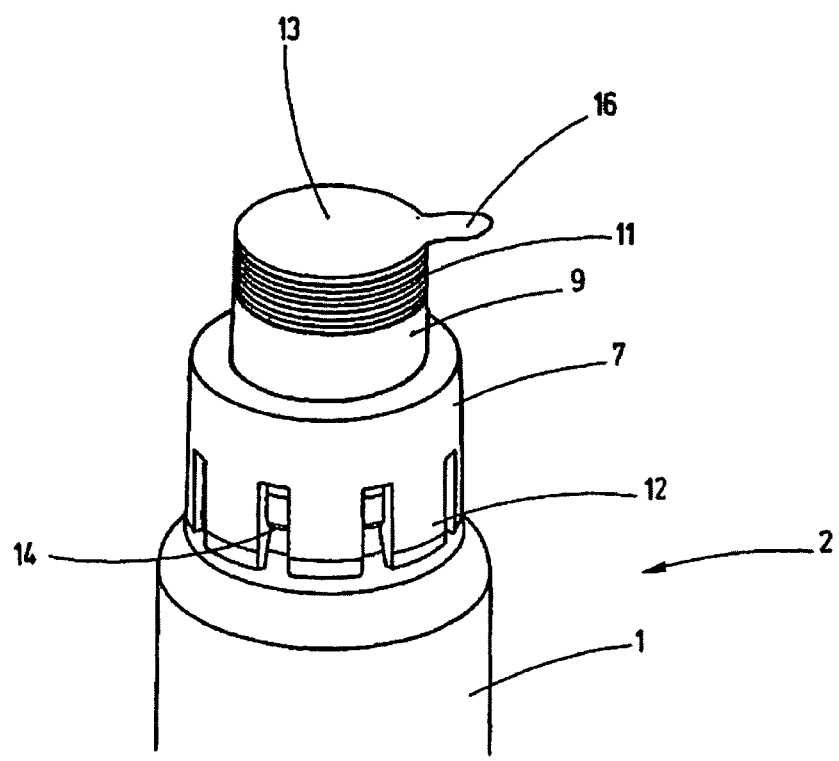
FIG. 2 is a perspective representation of an end of a cylinder that is covered with a sealing foil.

FIG. 2 shows a first embodiment of the syringe 2 with a cover device. Identical parts are provided with the same reference numbers so that in this respect we refer to the description of FIG. 1. The perspective representation shows that the cover device in this exemplary embodiment is embodied as sealing foil 13 applied to the lug 9. This sealing foil comprises a sealing area spanning the needle puncture area The syringe liquid in the cylinder 1 is sealed closed by the membrane 5, not visible in this figure. The membrane 5 is held on the end of the cylinder 1 by the closure element 7. This puncture area is spanned by the sealing foil 13 so that no contaminants can reach the still exposed area of the membrane 5, that is, the puncture area. The sealing foil 13 is attached to the closure element 7 of the cylinder 1 by means of an adhesive connection. The sealing foil 13, which is adhered onto the side of the lug 9 facing away from the cylinder, can include plastic and/or aluminum or can comprise these materials and preferably has at least one pull-off tab 16 at one point on the edge as a pull-off aid. The sealing foil 13 can thus be easily pulled off with this tab during use of the syringe 2. Subsequently, a needle can be inserted through the puncture area 18 into the cylinder 1. The important factor is that no axial forces act on the predetermined breaking line of the cap with this embodiment by using a two-part cap spanning the membrane.

Figure 3:
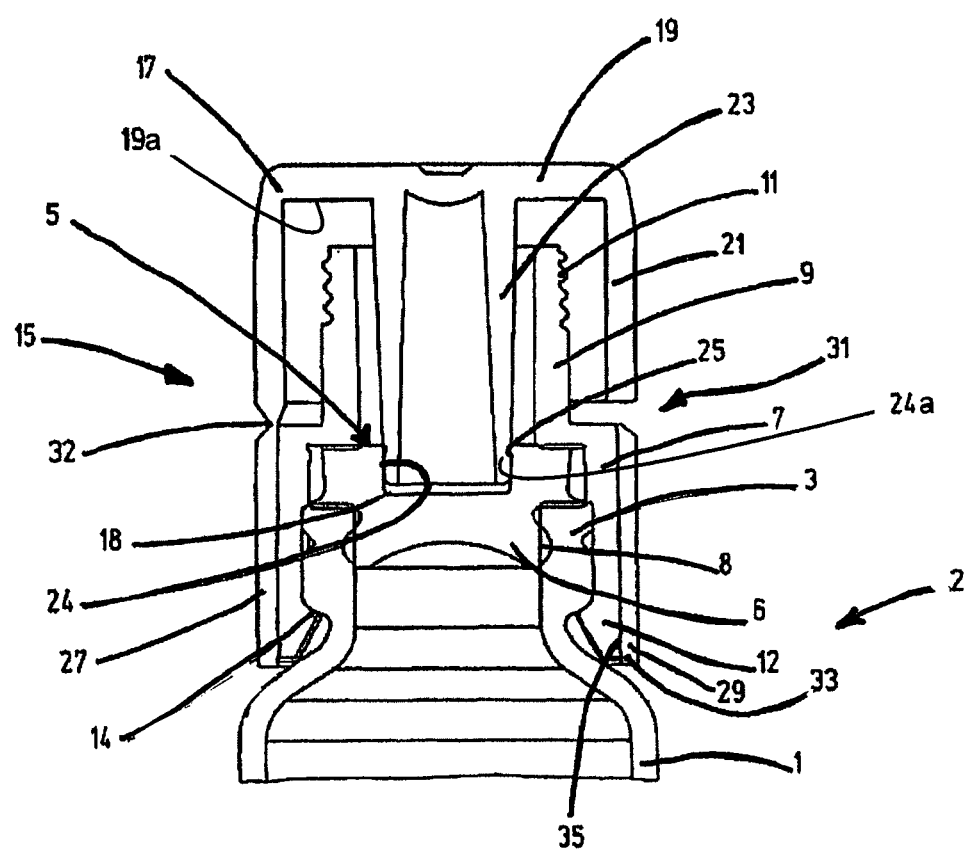
FIG. 3 is a longitudinal section of an end of a first exemplary embodiment of a syringe cylinder with a cap and a cover device.

FIG. 3 shows another embodiment. Identical parts are provided with the same reference numbers, so that in this respect reference is made to the description of the preceding figures. FIG. 3 shows the end 3 of the cylinder 1, the membrane 5 and the closure element 7, moreover, a two-part cap 15 spanning the membrane 5 and the closure element 7. This cap 15 has a first partial area 17, that has a base 19 with an inside wall 19a, a center jacket 21 starting therefrom and a centered projecting portion or tubular neck 23 extending perpendicularly from the inside wall 19a of the base 19. Furthermore, the membrane 5 has a recess 24, wherein the neck 23 of the first partial area 17 of the cap engages in the recess 24 of the membrane 5 through the lug 9, embodied in a hollow manner, of the closure element 7 and thus forms a projection. The puncture area 18 is a flat, planar portion of the membrane 5 which is formed by the base of the recess 24 of the membrane 5, and which is oriented perpendicularly to the neck 23. The outer diameter of the neck 23 and the inner diameter of the recess 24 are coordinated with one another such that the outer wall of the neck 23 bears against the inner wall of the recess 24 of the membrane 5 in a sealing manner.

Through this arrangement a cover device is therefore formed through the cap 15 and a sealing area is formed through the neck 23 and the recess 24, which have a projection and a recess accommodating the projection.

The sealing effect in the sealing area can be further improved in that at least one bead is provided on the outside of the projection realized here as the neck 23, and/or on the inside of the recess 24 accommodating the projection. In the exemplary embodiment shown in FIG. 3, a circumferential bead 25 is provided on a circumferential inside wall 24a of the recess 24 of the membrane 5, which bead projects radially inwards in the direction of an imaginary center axis of the recess 24.

A second partial area 27 of the two-part cap 15 is connected via a predefined breaking line 31 to the first partial area 17 of the cap 15. The predefined breaking line 31 can be realized by a thin-walled area. It is preferably provided for the two partial areas 17 and 27 of the cap 15 to be connected to one another by tear-off strips. A tear-off strip 32 of this type of the predetermined breaking point 31 can be seen in FIG. 3. The number of tear-off strips 32 can be adapted to the strength of the material of the cap 15 and to the forces acting on the cap 15 during transport and storage of the syringe 2.

The second partial area 27 can be connected to the closure element 7 for fixing to the end 3, for example, via an adhesive connection. The end 29, facing away from the first partial area 17, of the second partial area 27 of the cap 15—as shown here—preferably has at least one wedge-shaped projection 33 that engages in a recess 35 on the end 12, facing the cylinder 1, of the closure element 7 and thus serves to couple the second partial area 27 to the closure element 7.

The important factor is that no forces acting axially—that is in the direction of an imaginary central axis of the cap—occur on the predetermined breaking line 31. This ensures that tear-off strips 32 are not accidentally burst during the storage of the syringe 2. This prevents the first partial area 17 from being separated from the second partial area 27 and the puncture area 18 of the membrane 5 from being exposed. The axial forces are avoided in that a radial seal is formed by the bead 25 of the membrane 5, in that the bead 25 is pressed radially onto the outer surface of the neck 23 of the first partial area 17 of the cap 15.

Figure 4:
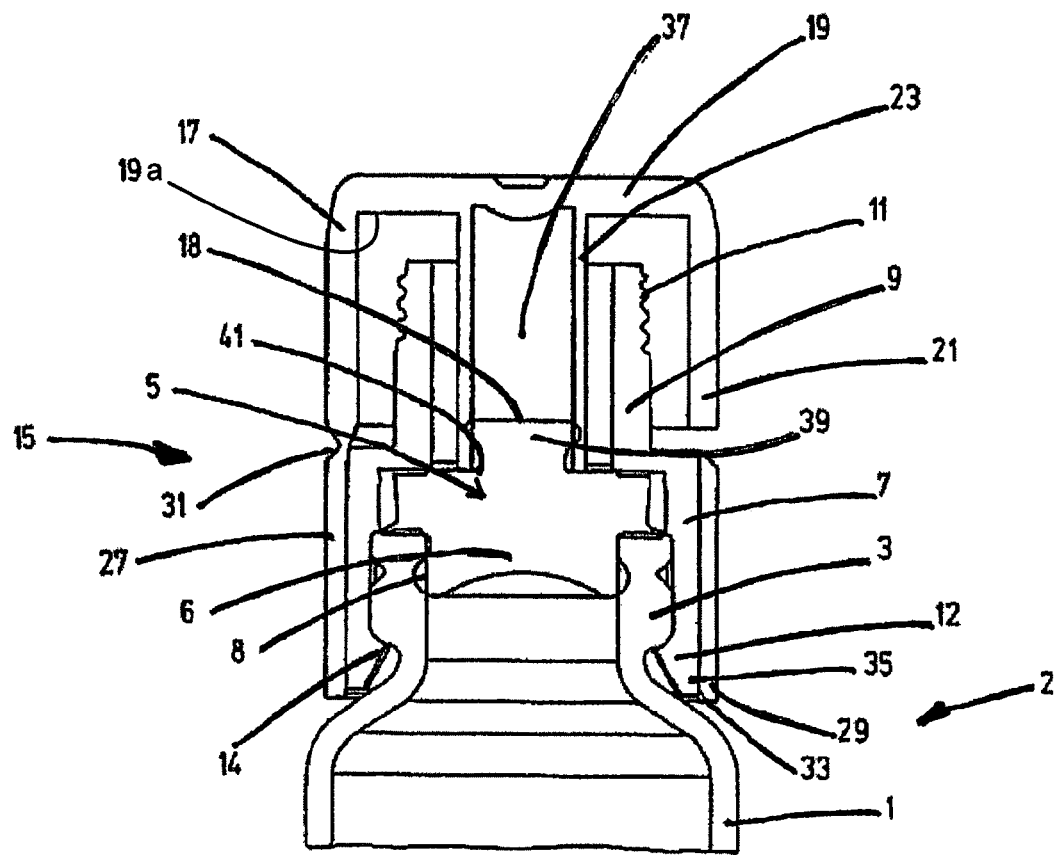
FIG. 4 is a longitudinal section of an end of a second exemplary embodiment of a cylinder with a cover device.

FIG. 4 shows another exemplary embodiment of the syringe 2. Identical parts are provided with the same reference numbers, so a repeated description has been omitted. In this embodiment the neck 23 has a recess 37, and the membrane 5 has a projection 39. The puncture area 18 forms a flat, planar surface and is located on the top of the projection 39 of the membrane 5, and is oriented perpendicular to the neck 23. The outer diameter of the projection 39 is coordinated with the inner diameter of the recess 37 of the neck 23 of the first partial area 17 of the two-part cap 15 such that a sealing area with a radial seal is realized in the contact area. The projection 39 of the membrane 5 preferably has at least one peripheral bead 41 projecting radially from the outer surface of the projection 39. Additionally, a radial compressive force is built up that improves the radial seal. Through the radial seal therefore no axial forces prevail at the predetermined breaking line 31, so it cannot be burst open.

Figure 5:
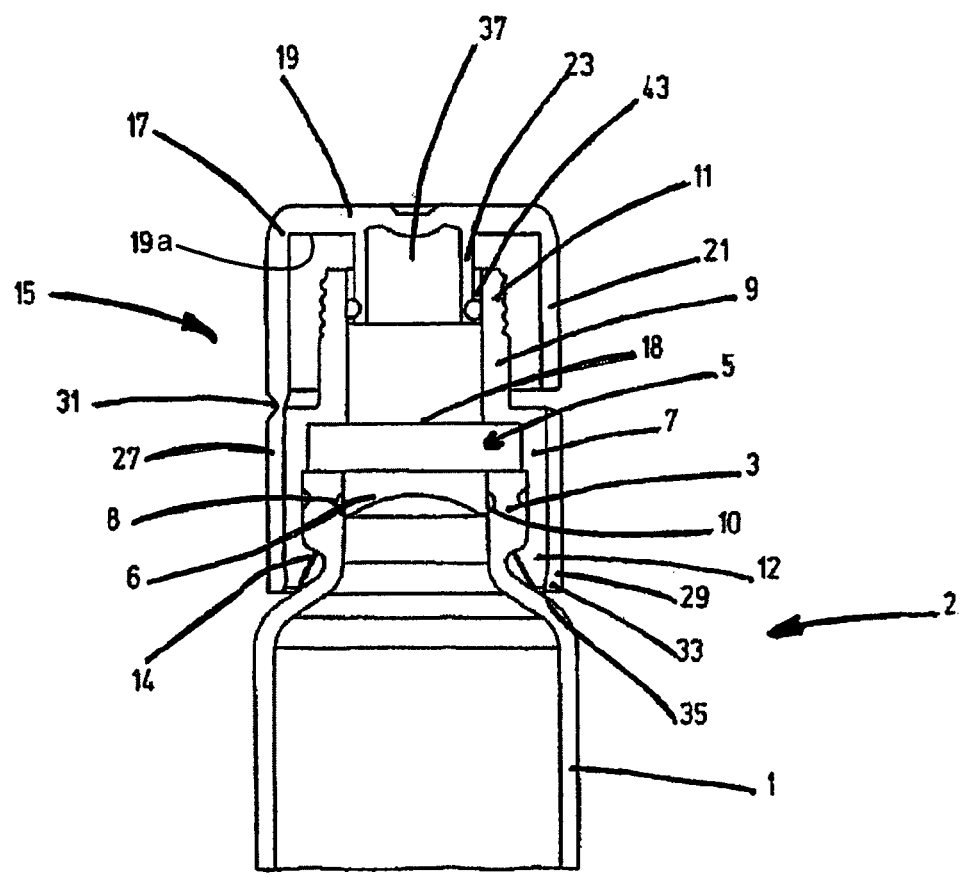
FIG. 5 is a longitudinal section of an end of a third exemplary embodiment of a cylinder.

FIG. 5 shows another embodiment of the syringe 2. Identical parts are provided with the same reference numbers, so a repeated description of the parts has been omitted. In this case, the neck 23 of the first partial area 17 of the two-part cap 15 can be embodied shorter. It engages in the interior of the lug 9. The outer diameter of the neck 23 can be coordinated with the inner diameter of the lug 9 such that a radial sealing area is created. At least one annular bead projecting radially from the outer surface of the neck 23 of the cap 15 can also be provided, which bead presses against the inner surface of the lug 9. However, a bead can also project radially from the inner surface of the lug 9 of the closure element 7 and press against the outer surface of the neck 23 in order to realize a sealing area.

Another possibility is for the sealing area to be realized by at least one separate sealing element—preferably embodied as an O-ring 43. This sealing element then lies between the inner surface of the lug 9 and the outer surface of the neck 23. To fix the position of the sealing element, an annular groove can be provided on the outer surface of the neck 23 and/or on the inner surface of the lug 9.

After all, it has been proven that in a simple manner the puncture area 18 of the membrane 5 can be covered in a sterile manner without requiring for this purpose any axial forces that would need to be applied to a cap 15. A predetermined breaking line 31 of the cap 15 in this manner remains unloaded and cannot tear open accidentally.

The cover device of the syringe 2 or carpule is thereby realized either by a sealing foil 13 that can be attached to the end 3 of the cylinder 1 by means of an adhesive connection. The adhesive connection can be realized by conventional adhesive or by ultrasonic bonding methods, heat or the like. The sealing foil 13 spans the puncture area 18 of the membrane 5 and protects it safely from contaminants.

The cover device and the sealing area thereof can also be realized in that a projection is provided on a cap 15 and/or the membrane 5 and accordingly a recess is provided on the membrane 5 and/or the cap 15. The projection has an outer surface, the outer diameter of which is coordinated with the inner diameter of the recess such that a radial seal is realized in the contact area. Axial are therefore not necessary forces to realize this seal.

The sealing action can be improved by at least one annular projection, that is, a bead, on the outside of the projection and/or the inside of the recess. Separate sealing elements, for example an O-ring 43, can also be provided in the contact area between the outer surface of the projection and the inner surface of the recess in order to realize the radial seal.

A consideration of the exemplary embodiment according to FIG. 5 shows that the length of the projection 23 and the length of the lug 29 measured in the direction of the imaginary central axis are coordinated with one another such that a radial sealing area is produced, either in that the outer surface of the projection 23 bears against the inner surface of the lug 9, or in that a bead is provided either on the outer surface of the projection 23 and/or the inner surface of the lug 9. Finally, the aforementioned O-ring 43 can also be provided to guarantee the radial seal. It is clear from FIG. 5 that the projection 23 does not need to be embodied in a hollow manner in the cases in which it is wrapped around by the lug 9.

In all it is shown that the cover device and the sealing area can be realized simply and cost-effectively and that the predetermined breaking line 31 of the cap 15 is no longer acted on by axial forces that could cause an accidental tearing of the predetermined breaking line, that is the tearing off of tear-off strips 32.

The invention claimed is:

1. An apparatus comprising:
   a cylinder surrounding a cavity and having an end that has an access to the cavity;
   a membrane sealing the access and a flat, planar puncture area that can be punctured by a needle, the membrane having one of a recess and a projection;
   a two-part cap having a predetermined break line, the two-part cap circumferentially surrounding the membrane and having a base portion with a tubular neck portion integrally formed with an inside wall of the base portion such that the tubular neck portion projects generally perpendicularly from the inside wall and perpendicular to the flat, planar puncture area;
   wherein the other of the recess and the projection is formed by the two-part cap such that the projection is received within the recess and a circumferential sealing bead associated with the membrane forms a radial seal with the tubular neck portion, and further wherein the radial seal is accomplished without requiring the two-part cap to apply an axial force between the tubular neck portion and the membrane, and without requiring contact of any part of the two-part cap with the flat, planar puncture area of the membrane,
   wherein the projection has an outer diameter less than an inner diameter of the access to the cavity.

2. The apparatus according to claim 1, wherein the two-part cap forms the projection and the membrane has the recess.

3. The apparatus according to claim 1, wherein the membrane has the projection and the two-part cap forms the recess.

* * * * *